(12) United States Patent
Sato et al.

(10) Patent No.: US 9,216,163 B2
(45) Date of Patent: Dec. 22, 2015

(54) METHOD OF INHIBITING ANGIOGENESIS

(71) Applicant: KYORIN PHARMACEUTICAL CO., LTD, Tokyo (JP)

(72) Inventors: Keizo Sato, Miyazaki (JP); Tomohiro Shinya, Miyazaki (JP); Shiori Nakayama, Miyazaki (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/196,247

(22) Filed: Mar. 4, 2014

(65) Prior Publication Data
US 2014/0343149 A1 Nov. 20, 2014

(30) Foreign Application Priority Data

May 20, 2013 (JP) ................................ 2013-105990

(51) Int. Cl.
*A61K 31/195* (2006.01)
*A61K 31/198* (2006.01)

(52) U.S. Cl.
CPC ............. *A61K 31/198* (2013.01); *A61K 31/195* (2013.01)

(58) Field of Classification Search
CPC .......................... A61K 31/195; A61K 31/198
USPC ................................................ 514/562, 563
See application file for complete search history.

(56) References Cited

U.S. PATENT DOCUMENTS

| | | | |
|---|---|---|---|
| 5,801,012 | A | 9/1998 | Soff et al. |
| 6,576,609 | B1 | 6/2003 | Soff et al. |
| 7,847,090 | B2 | 12/2010 | Reich et al. |
| 8,022,057 | B2 | 9/2011 | Dong et al. |
| 8,193,163 | B2 | 6/2012 | Reich et al. |
| 2004/0220129 | A1 | 11/2004 | Reich et al. |
| 2006/0099671 | A1 | 5/2006 | Soff et al. |
| 2009/0104260 | A1 | 4/2009 | Reich et al. |
| 2009/0124595 | A1 | 5/2009 | Adams et al. |
| 2011/0092571 | A1 | 4/2011 | Reich et al. |
| 2012/0276192 | A1 | 11/2012 | Reich et al. |

FOREIGN PATENT DOCUMENTS

| | | |
|---|---|---|
| JP | 2001-502534 | 2/2001 |
| JP | 2005-281229 | 10/2005 |
| JP | 2007-524349 | 8/2007 |
| JP | 2011-503099 | 1/2011 |
| JP | 2013-43851 | 3/2013 |

OTHER PUBLICATIONS

Macció et al., "Carbocysteine: clinical experience and new perspectives in the treatment of chronic inflammatory diseases", Expert Opinion on Pharmacotherapy, vol. 10, No. 4, pp. 693-703 (2009).*

Nakayama et al., "Novel reactions of L-Carbocisteine", The 85th Annual Meeting of the Japanese Biochemical Society, 2012, with English translation.
Shinya et al , "Inhibitory effects of L-carbocysteine on VEGF-induced angiogenesis", The 133rd Annual Meeting of the Pharmaceutical Society of Japan, 2013, with English translation.
Eriksson et al., "Angiostatin and endostatin inhibit endothelial cell migration in response to FGF and VEGF without interfering with specific intracellular signal transduction pathways", FEBS Letters, 2003, vol. 536, pp. 19-24.
Wu et al., "Involvement of COX-2 in VEGF-induced angiogenesis via P38 and JNK pathways in vascular endothelial cells", Cardiovascular Research, 2006, vol. 69, pp. 512-519.
Ha et al., "A Novel Role of Vascular Endothelial Cadherin in Modulating c-Src Activation and Downstream Signaling of Vascular Endothelial Growth Factor", The Journal of Biological Chemistry, 2008, vol. 283, pp. 7261-7270.
Nogawa, "Carbocisteine can scavenge reactive oxygen species in vitro", Respirology, 2009, vol. 14, pp. 53-59.
Cai et al., "N-Acetylcysteine Inhibits Endothelial Cell Invasion and Angiogenesis", Laboratory Investigation, 1999, vol. 79, No. 9, pp. 1151-1159.
Zhu et al., "Regulation of Angiogenesis by Vascular Endothelial Growth Factor and Angiopoietin-1 in the Rat Aorta Model", American Journal of Pathology, 2002, vol. 161, No. 3, pp. 823-830.
Agarwal et al., "N-Acetyl-Cysteine Promotes Angiostatin Production and Vascular Collapse in an Orthotopic Model of Breast Cancer", American Journal of Pathology, 2004, vol. 164, No. 5, pp. 1683-1696.
Okuno et al., "Pathological neoangiogenesis depends on oxidative stress regulation by ATM", Nature Medicine, 2012, vol. 18, No. 8, pp. 1208-1216.
Ishibashi et al., "Expression and Role of Sugar Chains on Airway Mucins, Especially in Induction and Exacerbation of Airway Inflammation", Inflammation and Regeneration, 2007, vol. 27, No. 3, pp. 177-183.
Albini et al , "Inhibition of Angiogenesis-driven Kaposi's Sarcoma Tumor Growth in Nude Mice by Oral N-Acetylcysteine", Cancer Research, 2001, vol. 61, pp. 8171-8178.
McMahon, "VEGF Receptor Signaling in Tumor Angiogenesis", The Oncologist, 2000, vol. 5, pp. 3-10.
Zachary et al., "Signaling transduction mechanisms mediating biological actions of the vascular endothelial growth factor family", Cardiovascular Research, 2001, vol. 49, No. 3, pp. 568-581.
Pratheeshkumar et al., "Luteolin Inhibits Human Prostate Tumor Growth by Suppressing Vascular Endothelial Growth Factor Receptor 2-Mediated Angiogenesis", PLoS One, 2012, vol. 7, No. 12, pp. e52279.
Takahashi, "Vascular Endothelial Growth Factor (VEGF), VEGF Receptors and Their Inhibitors for Antiangiogenic Tumor Therapy", Biol. Pharm. Bull., 2011, vol. 34, No. 12, pp. 1785-1788.

(Continued)

*Primary Examiner* — Kevin E Weddington
(74) *Attorney, Agent, or Firm* — Wenderoth, Lind & Ponack, L.L.P.

(57) ABSTRACT

A novel angiogenesis inhibitor, and a method for inhibiting angiogenesis are provided. Also provided are a prophylactic or therapeutic agent for a disease accompanied by angiogenesis, and a method for preventing or treating a disease accompanied by angiogenesis. The angiogenesis inhibitor contains L-carbocisteine or a pharmaceutically acceptable salt thereof as an active ingredient.

3 Claims, 4 Drawing Sheets

(56) References Cited

OTHER PUBLICATIONS

Takahashi et al., "The 230 kDa mature form of KDR/Flk-1 (VEGF receptor-2) activates the PLC-γ pathway and partially induces mitotic signals in NIH3T3 fibroblasts", Oncogene, 1997, vol. 14, No. 17, pp. 2079-2089.
Takeda et al., "S-carboxymethylcysteine normalises airway responsiveness in sensitised and challenged mice", European Respiratory Journal, 2005, vol. 26, No. 4, pp. 577-585.
Yamaya et al , "Inhibitory effects of carbocisteine on type A seasonal influenza virus infection in human airway epithelial cells", American Journal of Physiology Lung Cellular and Molecular Physiology, 2010, vol. 299, No. 2, pp. L160-L168.
Asada et al., "L-carbocisteine inhibits respiratory syncytial virus infection in human tracheal epithelial cells", Respiratory Physiology & Neurobiology, 2012, vol. 180, No. 1, pp. 112-118.
Yasuda et al., "Carbocisteine inhibits rhinovirus infection in human tracheal epithelial cells", European Respiratory Journal, 2006, vol. 28, No. 1, pp. 51-58.
Dellinger et al., "Phosphorylation of Akt and ERK1/2 Is Required for VEGF-A/VEGFR2-Induced Proliferation and Migration of Lymphatic Endothelium", PLoS One, 2011, vol. 6, No. 12, pp. e28947.
Shibuya, "VEGF-VEGFR Signals in Health and Disease", Biomol. Ther., 2014, vol. 22, No. 1, pp. 1-9.
Shibuya, "Vascular endothelial growth factor and its receptor system: physiological functions in angiogenesis and pathological roles in various diseases", Journal of Biochemistry, 2013, vol. 153, No. 1, pp. 13-19.
Claesson-Welsh, "Blood vessels as targets in tumor therapy", Upsala Journal of Medical Sciences, 2012, vol. 117, No. 2, pp. 178-186.
Sceneay et al., "The Antioxidant N-Acetylcysteine Prevents HIF-1 Stabilization Under Hypoxia In Vitro but Does Not Affect Tumorigenesis in Multiple Breast Cancer Models In Vivo", PLoS One, 2013, vol. 8, No. 6, pp. e66388.
Hooper et al., "The role for S-carboxymethylcysteine (carbocisteine) in the management of chronic obstructive pulmonary disease", International Journal of COPD, 2008, vol. 3, No. 4, pp. 659-669.
Nagy et al., "VEGF-A and the Induction of Pathological Angiogenesis", Annual Review of Pathology: Mechanisms of Disease, 2007, vol. 2, pp. 251-275.
Wu et al., "Utilization of Distinct Signaling Pathways by Receptors for Vascular Endothelial Cell Growth Factor and Other Mitogens in the Induction of Endothelial Cell Proliferation", Journal of Biological Chemistry, 2000, vol. 275, No. 7, pp. 5096-5103.
Murphy et al , "Inhibition of Tumor Endothelial ERK Activation, Angiogenesis, and Tumor Growth by Sorafenib (BAY43-9006)", The American Journal of Pathology, 2006, vol. 169, No. 5, pp. 1875-1885.
Wedge et al., "ZD6474 Inhibits Vascular Endothelial Growth Factor Signaling, Angiogenesis, and Tumor Growth Following Oral Administration", Cancer Research, 2002, vol. 62, No. 16, pp. 4645-4655.
Weng et al., "Flavonoids, a ubiquitous dietary phenolic subclass, exert extensive in vitro anti-invasive and in vivo anti-metastatic activities", Cancer Metastasis Rev., 2012, vol. 31, pp. 323-351.
Cho et al., "Kisspeptin-10, a KISS1-Derived Decapeptide, Inhibits Tumor Angiogenesis by Suppressing Sp1-Mediated VEGF Expression and FAK/Rho GTPase Activation", Cancer Research, 2009, vol. 69, No. 17, pp. 7062-7070.
Yang et al., "Anti-Cancer Activity of an Osthole Derivative, NBM-T-BMX-OS01: Targeting Vascular Endothelial Growth Factor Receptor Signaling and Angiogenesis", PLoS One, 2013, vol. 8, No. 11, pp. e81592.
Kwon et al., "Phloroglucinol Inhibits the Bioactivities of Endothelial Progenitor Cells and Suppresses Tumor Angiogenesis in LLC-Tumor-Bearing Mice", PLoS One, 2012, vol. 7, No. 4, pp. e33618.
Feleszko et al., "Lovastatin Potentiates Antitumor Activity and Attenuates Cardiotoxicity of Doxorubicin in Three Tumor Models in Mice", Clinical Cancer Research, 2000, vol. 6, No. 5, pp. 2044-2052.
Dai et al., "A Natural Small Molecule Harmine Inhibits Angiogenesis and Suppresses Tumour Growth Through Activation of p53 in Endothelial Cells", PLoS One, 2012, vol. 7, No. 12, pp. e52162.
Mallet et al., "Respiratory Paradoxical Adverse Drug Reactions Associated with Acetylcysteine and Carbocysteine Systemic Use in Paediatric Patients: A National Survey", PLoS One, 2011, vol. 6, No. 7, pp. e22792.
Takeuchi et al., "Mitogen-activated protein kinase phosphatase-1 modulated JNK activation is critical for apoptosis induced by inhibitor of epidermal growth factor receptor-tyrosine kinase", FEBS Journal, 2009, vol. 276, No. 5, pp. 1255-1265.
Yang et al., "Celastrol, a Triterpene Extracted from the Chinese 'Thunder of God Vine,' is a Potent Proteasome Inhibitor and Suppresses Human Prostate Cancer Growth in Nude Mice", Cancer Research, 2006, vol. 66, No. 9, pp. 4758-4765.
Pang et al., "Celastrol Suppresses Angiogenesis-Mediated Tumor Growth Through Inhibition of AKT/Mammalian Target of Rapamycin Pathway", Cancer Research, 2010, vol. 70, No. 5, pp. 1951-1959.
Stehn et al., "A Novel Class of Anticancer Compounds Targets the Actin Cytoskeleton in Tumor Cells", Cancer Research, 2013, vol. 73, No. 16, pp. 5169-5182.
Pang et al., "Morelloflavone, a Biflavonoid, Inhibits Tumor Angiogenesis by Targeting Rho GTPases and Extracellular Signal-Regulated Kinase Signaling Pathways", Cancer Research, 2009, vol. 69, No. 2, pp. 518-525.
Bhat et al., "Tumor angiogenesis—A Potential Target in Cancer Chemoprevention", Food and Chemical Toxicology, 2008, vol. 46, No. 4, pp. 1334-1345.
Takahashi et al., "A single autophosphorylation site on KDR/Flk-1 is essential for VEGF-A-dependent activation of PLC-γ and DNA synthesis in vascular endothelial cells", EMBO Journal, 2001, vol. 20, No. 11, pp. 2768-2778.
Yi et al., "Thymoquinone inhibits tumor angiogenesis and tumor growth through suppressing AKT and extracellular signal-regulated kinase signaling pathways", Molecular Cancer Therapy, 2008, vol. 7, No. 7, pp. 1789-1796.

\* cited by examiner

METHOD OF INHIBITING ANGIOGENESIS

BACKGROUND OF THE INVENTION

1. Field of the Invention

The present invention relates to suppression of angiogenesis.

2. Description of the Related Art

Angiogenesis is a physiological phenomenon in the human body of healthy adults, and "a process of forming new blood vessels from existing vessels in the body." Therefore, angiogenesis is a physiological phenomenon necessary, for the body.

However, the angiogenesis for supply of nutrients to tumor in tumor growth and metastasis or to hypertrophied tissues in tissue hypertrophy is confirmed, in tumor diseases, various ophthalmic diseases, chronic inflammation, or other diseases such as cancer, age-related macular degeneration, diabetic retinopathy, psoriasis, rheumatoid arthritis and osteoarthritis.

For these reasons, it is considered that these diseases can be prevented or treated by restoring the balance to a moderate state in healthy subjects between "angiogenesis" and "suppression of angiogenesis".

In recent years, an inhibitor of vascular endothelial growth factor (VEGF) which is known as the promoting factor of angiogenesis, that is, a kind of angiogenesis inhibitor has been clinically applied. Examples of the VEGF inhibitor may include an anti-VEGF antibody and an anti-VEGF aptamer. By using these compounds, it was confirmed that the effectiveness of the angiogenesis inhibitor as a therapeutic agent for some kinds of cancer diseases, diabetic retinopathy, or age-related macular degeneration. However, it has been reported that the existing VEGF inhibitors have disadvantages such as side effects including hemorrhage, hypertension, and cardiotoxicity, low reproducibility of their effect, and variation of their effect depending on the species. For these disadvantages, it is sometimes difficult to administer the existing angiogenesis inhibitors to a patient.

Antioxidants such as vitamin C, vitamin E, and flavonoid are also known as compounds having an angiogenesis inhibitory effect. However, since the molecular weight of the compounds is high, these compounds have problems such as low absorption and low intercellular penetration. Therefore, these compounds seem to be less suitable for practical use.

PRIOR ART LITERATURES

Patent Literature

[Patent Literature 1] JP2013-43851
[Non-Patent Literature 1] FEBS Letters 536(1-3): 19-24, 2003
[Non-Patent Literature 2] Cardiovascular Research 69(2): 512-520, 2006
[Non-Patent Literature 3] The Journal of Biological Chemistry 283(11): 7261-7270, 2008
[Non-Patent Literature 4] Respirology 14(1): 53-50, 2009

SUMMARY OF THE INVENTION

For these reasons described above, the development of an angiogenesis inhibitor which has higher safety, an improved kinetic profile, and a low molecular weight is expected.

An object of the present invention is to provide a novel angiogenesis inhibitor, and a prophylactic or therapeutic agent for a disease accompanied by angiogenesis.

The present inventor has studied a method for preventing or treating a disease based on suppression of angiogenesis. In this study, the present inventor has investigated an effect on angiogenesis of L-carbocisteine, which is widely known as an expectorant, in systems for evaluation of the anti-angiogenesis using normal human umbilical vein endothelial cells (HUVEC) in vitro and an animal injected with matrigel in vivo. As a result, a marked antiangiogenic effect of L-carbocisteine is observed.

Angiogenesis is promoted by stimulation of VEGF. It is known that this promotion is caused by accelerated phosphorylation of Akt, Erk1/2, JNK, and p38 MAPK (Non-Patent Literatures 1 to 3). As described in detail in Examples, L-carbocisteine suppresses signal transduction upstream of Erk1/2. Specifically, the present inventor has found that L-carbocisteine inhibits the effect of VEGF through the suppression of signal transduction caused by VEGF, resulting in the suppression of angiogenesis caused by VEGF stimulation.

L-carbocisteine is a cysteine derivative and used as an expectorant. L-carbocisteine has been developed by Laboratoires Joulie in France, and a pharmaceutical containing L-carbocisteine has been commercialized under a trade name "Rhinathiol" since 1965. In United Kingdom, a pharmaceutical containing L-carbocisteine has been commercialized by Berk Pharmaceuticals under a trade name "Mucodyne" since 1972.

In countries of the world, a pharmaceutical containing L-carbocisteine has been commercialized currently.

Also in Japan, a pharmaceutical containing L-carbocisteine has been developed by KYORIN Pharmaceutical Co., Ltd., approved for marketing by the Ministry of Health, Labour and Welfare, and commercialized under a trade name "MUCODYNE (registered trademark)" since 1981. Since then, MUCODYNE has been widely used in clinical application as an expectorant having high safety.

It is known that L-carbocisteine has various effects including (1) improving physical properties of sputum to rapidly discharge the sputum, (2) promoting the repair of mucociliary to improve its transport performance, and (3) suppressing the attachment of bacteria to pharyngeal epithelial cells as a first step for bacterial infection. L-carbocisteine has a limited and weak antioxidative effect (Non-Patent Literature 4), which is partially mediated by activation of Nrf2 (Patent Literature 1). However, L-carbocisteine exhibits an antiangiogenic effect which is comparable (not inferior) to N-acetylcysteine exhibiting a strong antioxidative effect and suppresses phosphorylation with a short time-course. Therefore, a property other than the antioxidative effect is possible to be involved in the antiangiogenic effect of L-carbocisteine.

Specifically, aspects of the present invention can include as follows:

[1] An angiogenesis inhibitor comprising L-carbocisteine or a pharmaceutically acceptable salt thereof as an active ingredient.

[2] A prophylactic or therapeutic agent for a disease accompanied by angiogenesis, comprising L-carbocisteine or a pharmaceutically acceptable salt thereof as an active ingredient.

[3] The prophylactic or therapeutic agent according to [2], wherein the disease accompanied by angiogenesis is diabetic retinopathy or age-related macular degeneration.

[4] The prophylactic or therapeutic agent according to [2], wherein the disease accompanied by angiogenesis is a tumor disease.

[5] An agent for suppressing tumor growth or metastasis caused by a tumor disease accompanied by angiogenesis, comprising L-carbocisteine or a pharmaceutically acceptable salt thereof as an active ingredient.

[6] An inhibitor of signal transduction caused by a vascular endothelial growth factor, comprising L-carbocisteine or a pharmaceutically acceptable salt thereof as an active ingredient.

[7] A method for inhibiting angiogenesis, comprising administering L-carbocisteine or a pharmaceutically acceptable salt thereof in an amount effective to inhibit angiogenesis to a patient in need thereof.

[8] A method for preventing or treating a disease accompanied by angiogenesis, comprising administering L-carbocisteine or a pharmaceutically acceptable salt thereof in an amount effective to prevent or treat a patient in need thereof.

[9] The method according to [8], wherein the disease accompanied by angiogenesis is diabetic retinopathy or age-related macular degeneration.

[10] The method according to [8], wherein the disease accompanied by angiogenesis is a tumor disease.

[11] The method according to [10], wherein the method is for treating a tumor disease comprising administering L-carbocisteine to suppress tumor growth or metastasis.

[12] A method for inhibiting signal transduction caused by a vascular endothelial growth factor, comprising administering L-carbocisteine or a pharmaceutically acceptable salt thereof in an amount effective to inhibit the vascular endothelial growth factor to a patient in need thereof.

The present invention can provide a novel angiogenesis inhibitor, and a prophylactic or therapeutic agent for a disease accompanied by angiogenesis.

DETAILED DESCRIPTION OF THE PREFERRED EMBODIMENT

Figure 1:
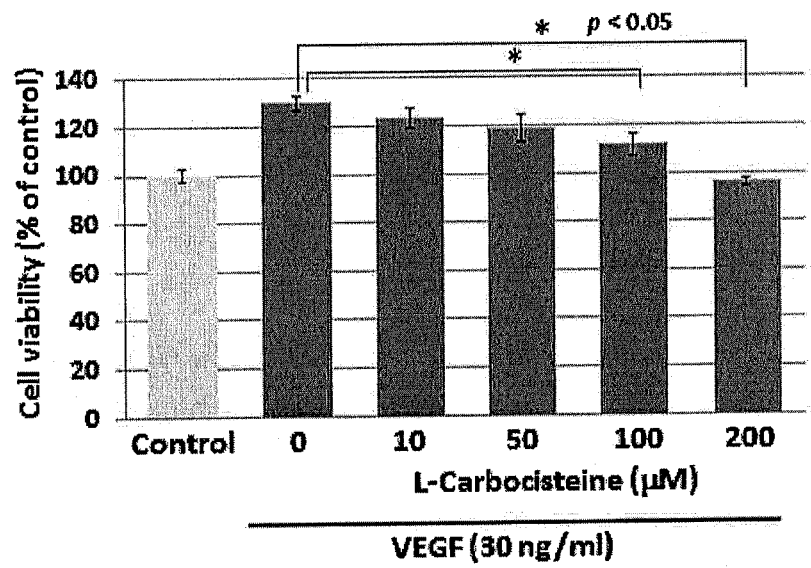
FIG. 1 is a graph showing an effect of L-carbocisteine (10, 50, 100, and 200 μM) against VEGF-induced cell growth of HUVEC in Example 1.
Figure 2:
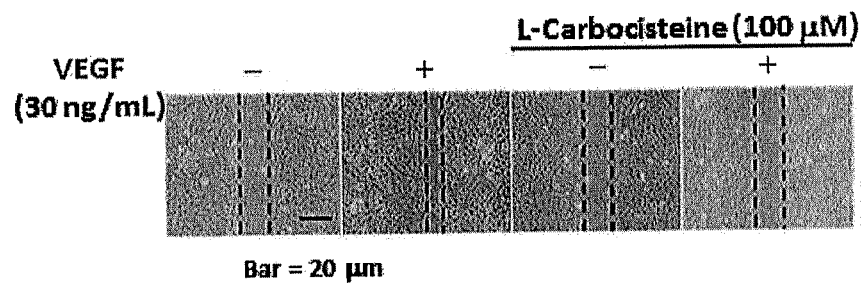
FIG. 2 is a photograph showing an effect of L-carbocisteine (100 μM) against VEGF-induced cell migration of HUVEC in Example 2.
Figure 3:
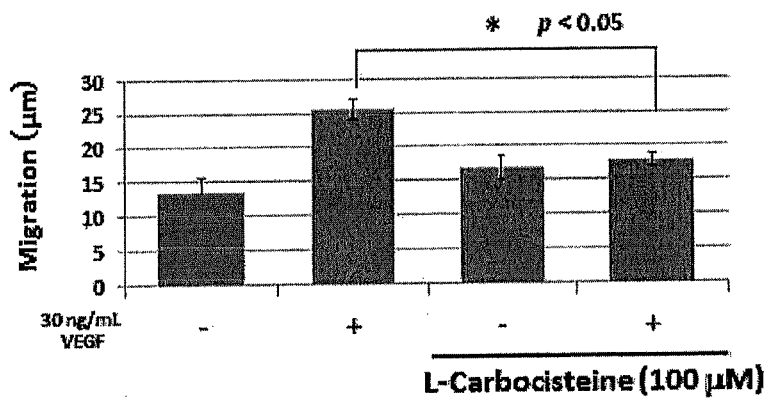
FIG. 3 is a graph illustrating the effect of L-carbocisteine (100 μM) against VEGF-induced cell migration of HUVEC in Example 2.
Figure 4:
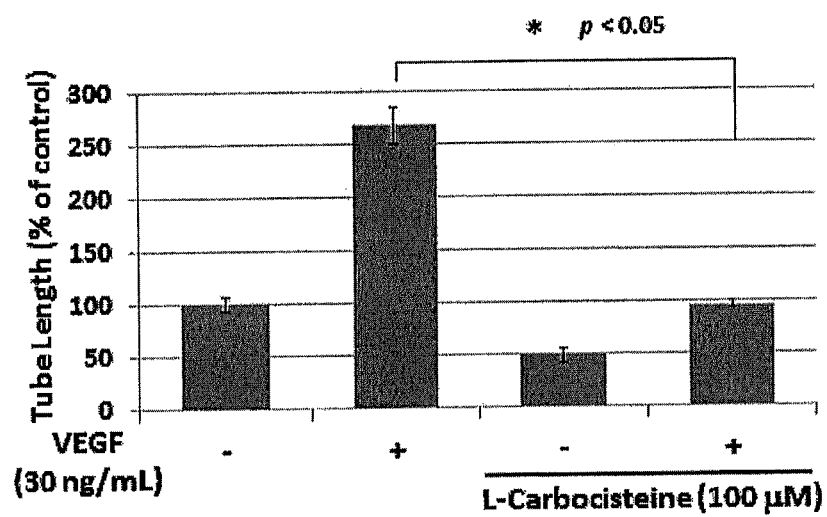
FIG. 4 is a graph illustrating an effect of L-carbocisteine (100 μM) against VEGF-induced tube formation of HUVEC in Example 3.
Figure 5:
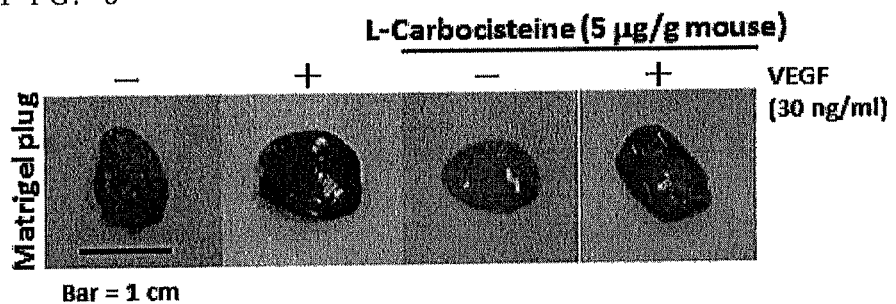
FIG. 5 is a photograph showing an effect of L-carbocisteine (5 μg/g of body weight) against VEGF-induced angiogenesis formed in Matrigel in Example 4.
Figure 6:
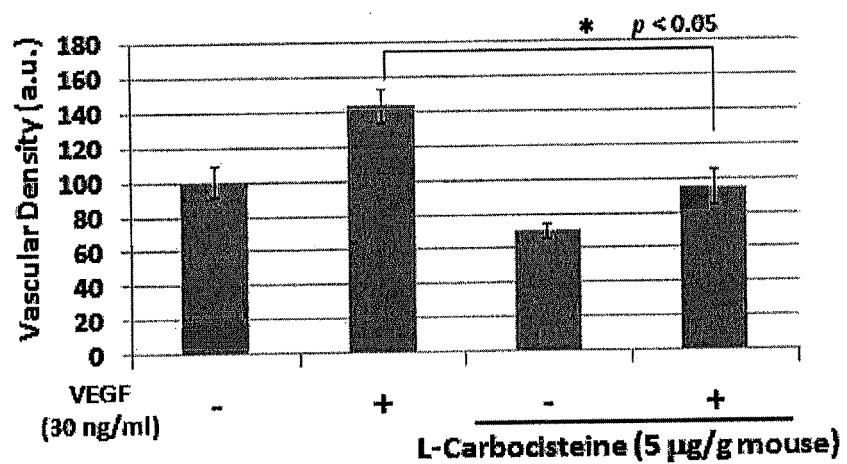
FIG. 6 is a graph illustrating the effect of L-carbocisteine (5 μg/g of body weight) against VEGF-induced angiogenesis formed in Matrigel in Example 4.
Figure 7:
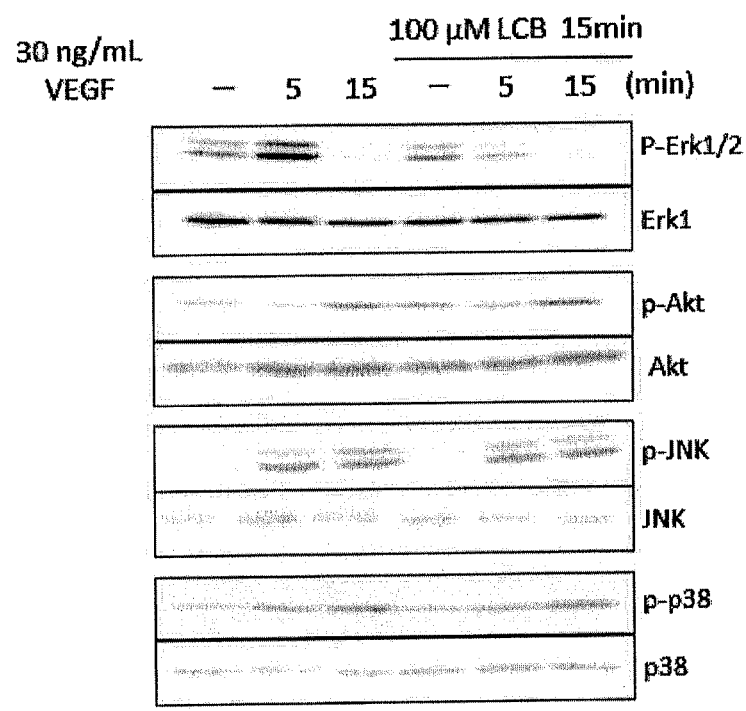
FIG. 7 is a photograph showing an effect of L-carbocisteine (100 μM) against VEGF-induced phosphorylation of each protein in HUVEC in Example 5.

Hereinafter, an embodiment of the present invention will be described in more detail, but the present invention is not limited to the embodiment.

An angiogenesis inhibitor of an embodiment contains L-carbocisteine or a pharmaceutically acceptable salt thereof as an active ingredient.

L-carbocisteine is a compound also referred to as S-(carboxymethyl)-L-cysteine, its chemical name. L-carbocisteine is represented by the following formula (1).

[Chemical Formula 1]

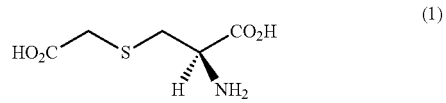

(1)

A pharmaceutically acceptable salt of L-carbocisteine represents a salt of L-carbocisteine with a pharmaceutically acceptable base or acid. The pharmaceutically acceptable base may be any of an inorganic base and an organic base. Similarly, the pharmaceutically acceptable acid may be any of an inorganic acid and an organic acid.

Examples of a salt with a pharmaceutically acceptable inorganic base may include salts with inorganic bases such as aluminum, ammonium, calcium, copper, ferrous iron, ferric iron, lithium, magnesium, manganese, manganous acid, potassium, and sodium.

Examples of a salt with a pharmaceutically acceptable organic base may include salts with organic bases such as arginine, betaine, caffeine, choline, N,N'-dibenzylethylene diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, a polyamine resin, procaine, purine, theobromine, triethylamine, trimethylamine, tripropylamine, and tromethamine.

Examples of a salt with a pharmaceutically acceptable inorganic acid may include salts with inorganic acids such as hydrochloric acid, hydrobromic acid, sulfuric acid, and nitric acid.

Examples of a salt with a pharmaceutically acceptable organic acid may include salts with organic acids such as acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

The angiogenesis inhibitor of the present embodiment may contain L-carbocisteine or a pharmaceutically acceptable salt thereof solely/alone. Further, the angiogenesis inhibitor of the present embodiment may be constituted as a pharmaceutical composition containing L-carbocisteine, and another compound acting as an active ingredient and/or a pharmaceutically acceptable additive. The pharmaceutical composition contains one or more compounds as the other compound acting as an active ingredient and/or as the pharmaceutically acceptable additive. The pharmaceutical composition is prepared, for example, by mixing L-carbocisteine, and one or more of the other compounds acting as an active ingredient and/or an additive.

Examples of the other compound acting as an active ingredient, to be mixed with L-carbocisteine, in the pharmaceutical composition may include an angiogenesis inhibitor, an anticancer agent, and an anti-inflammatory agent.

Examples of the pharmaceutically acceptable additive, to be mixed with L-carbocisteine, in the pharmaceutical composition may include an excipient, a lubricant, a binder, a disintegrant, stabilizer, a corrective, and a diluent. These additives are not particularly limited as long as they can be used for production of a pharmaceutical preparation, and for example, additives listed in "Japanese Pharmaceutical Excipients Directory (International Pharmaceutical Excipients Council Japan, YAKUJI NIPPO, LTD. (2007))" can be appropriately used.

The angiogenesis inhibitor of the present embodiment can be administered to human in a form conventionally well known as a pharmaceutical form through an administration route conventionally well known as a pharmaceutical route. For example, the angiogenesis inhibitor can be orally administered in a form of preparation such as a powder, a tablet, a capsule, a fine granule, a granule, and a syrup. Further, the angiogenesis inhibitor can be parenterally administered in a preparation form such as an ophthalmic solution.

The dose of L-carbocisteine in the angiogenesis inhibitor of the present embodiment is not particularly limited, and can be varied depending on a preparation form, the age, symptom, or the like, of a patient as a subject to be administered. For example, the dose of L-carbocisteine may be set to 1.5 g/day or more and 15 g/day or less, and preferably 1.5 g/day or more and 5 g/day or less.

L-carbocisteine according to the present embodiment significantly suppresses cell growth, cell migration, and tube formation of endothelial cells induced by VEGF in vitro, which are involved in angiogenesis and markedly inhibits angiogenesis induced by VEGF in vivo.

Therefore, the angiogenesis inhibitor of the present embodiment is effective in prevention or treatment for a disease accompanied by angiogenesis. Examples of such a disease may include age-related macular degeneration, diabetic retinopathy, proliferative diabetic retinopathy, retinopathy of prematurity, neovascular glaucoma, obstruction of retinal vein, obstruction of retinal artery, pterygium, rubeosis, corneal angiogenesis, a tumor disease (brain tumor, pharyngeal cancer, lung cancer, gastric cancer, colon cancer, colorectal cancer, liver cancer, pancreatic cancer, renal cell cancer, prostate cancer, bladder cancer, breast cancer, and ovarian cancer), myeloma, hemangioma, rheumatoid arthritis, psoriasis, and osteoarthritis.

In particular, the angiogenesis inhibitor of the present embodiment is useful as an agent for suppressing tumor growth and metastasis in the disease accompanied by angiogenesis.

The present embodiment can provide an angiogenesis inhibitor which has less side effect by use of L-carbocisteine as compared with the existing angiogenesis inhibitor.

The present embodiment can also provide an angiogenesis inhibitor which has improved kinetic profile as compared with the existing antioxidant.

EXAMPLES

Hereinafter, the present invention will be further described byway of Examples. However, the present invention is not limited to these examples.

Example 1

An effect of L-carbocisteine against cell growth promotion by VEGF was evaluated in vitro using HUVEC.
1) Procedure
HUVEC were inoculated at 2,500 cells/well in a 96-well microplate, and cultured for 24 hours.
Subsequently, the HUVEC were cultured in a medium without VEGF and bFGF overnight under a starvation condition. The HUVEC were pretreated with L-carbocisteine (10, 50, 100, and 200 μM) for 15 minutes, and then stimulated by VEGF (30 ng/mL). The number of living cells after 48 hours was determined by Cell Counting Kit-8 (manufactured by DOJINDO LABORATORIES) (n=6).

2) Results
By the pretreatment with 100 μM or more of L-carbocisteine, the endothelial cell growth promoted by VEGF was significantly suppressed. The growth suppressive effect of L-carbocisteine was concentration-dependent.

Example 2

An effect of L-carbocisteine against cell migration promoted by VEGF was evaluated in vitro using HUVEC.
1) Procedure
HUVEC were inoculated in a plate, and cultured until confluent. Subsequently, the HUVEC were cultured in a medium without VEGF and bFGF overnight under starvation condition. The HUVEC were pretreated with L-carbocisteine (100 μM) for 15 minutes. The cells (HUVEC) on the plate were peeled at certain intervals. The cells remaining on the plate were stimulated by VEGF (30 ng/mL). After 12 hours, the distance of cell migration was measured (n=4).
2) Results
By the pretreatment with L-carbocisteine, the migration promoted by VEGF was significantly suppressed.

Example 3

An effect of L-carbocisteine against tube formation promoted by VEGF was evaluated in vitro using HUVEC.
1) Procedure
A collagen Type 1-C (available from Nitta Gelatin Inc.) lower layer was formed on a 12-well plate, HUVEC were inoculated on the lower layer, and a collagen upper layer was then formed. The HUVEC were pretreated with L-carbocisteine (100 μM) for 15 minutes, and stimulated by VEGF (30 ng/mL). The overall length of the lumen after 24 hours was measured (n=6).
2) Results
By the pretreatment with L-carbocisteine, the tube formation promoted by VEGF was significantly suppressed.

Example 4

An effect of L-carbocisteine against angiogenesis promoted by VEGF was evaluated in an in vivo mouse model.
1) Procedure
A male C57BL/6J mouse (6 weeks) was anesthetized with pentobarbital. Subsequently, 500 μL of BD™ matrix containing 30 ng/mL VEGF was subcutaneously injected into the side of the mouse using a 27-G needle. L-carbocisteine (5 μg per g of body weight of the mouse) or physiologic saline (the same volume) was intraperitoneally administered twice a day, morning and evening, for 14 days. After completion of the administration for 14 days, Evans blue was administered to the mouse via the orbital vein plexus. The mouse was sufficiently perfused with EDTA, and anesthetized with pentobarbital. The matrigel was taken out from the body of the mouse. The weight of taken matrigel was measured, and the matrigel was immersed in a formamide solution and allowed to stand at 37° C. for 48 hours. Following elution of Evans blue in the formamide solution, the weight of eluted Evans blue per unit weight of the matrigel was measured using an absorbance of 620 nm (n=8).
2) Results
The vascular density in the matrigel was markedly decreased by the intraperitoneal administration of L-carbocisteine (5 μg/g B.W.) twice daily.

Example 5

An effect of L-carbocisteine against phosphorylation of Akt, Erk1/2, c-Jun N-terminal kinase (JNK), and p38 MAP kinase accelerated by VEGF stimulation was evaluated using HUVEC.

1) Procedure

HUVEC were inoculated, and cultured in an EBM-2 medium containing 0.1% FBS overnight under starvation condition. The HUVEC were pretreated with L-carbocisteine (100 μM) for 15 minutes, and stimulated by VEGF (30 ng/mL) for 5 or 15 minutes. Phosphorylation accelerated by VEGF stimulation was evaluated using phosphor-specific antibodies against various kinases by a Western blot method. The level of kinase protein expression was investigated using each antibody after detection of phosphorylation.

2) Results

By VEGF stimulation, phosphorylation of Erk1/2, JNK, and p38 MAP kinase was accelerated in 5 minutes, and phosphorylation of Akt was accelerated in 15 minutes. Among them, only accelerated phosphorylation of Erk1/2 was specifically suppressed by L-carbocisteine.

L-carbocisteine according to the present invention is useful, for example, as a prophylactic or therapeutic agent for a disease accompanied by angiogenesis.

What is claimed is:

1. A method for treating a disease accompanied by angiogenesis, comprising administering L-carbocisteine or a pharmaceutically acceptable salt thereof in an amount effective to treat a patient in need thereof, wherein the disease accompanied by angiogenesis is diabetic retinopathy or age-related macular degeneration.

2. A method for treating a disease accompanied by angiogenesis, comprising administering L-carbocisteine or a pharmaceutically acceptable salt thereof in an amount effective to treat a patient in need thereof, wherein the disease accompanied by angiogenesis is a tumor disease.

3. The method according to claim 2, wherein the method is for treating a tumor disease including administering L-carbocisteine to suppress tumor growth or metastasis.

* * * * *